(12) United States Patent
Eastman

(10) Patent No.: US 10,295,514 B1
(45) Date of Patent: May 21, 2019

(54) INSTRUMENT AND METHOD FOR SEALED PENETRATION OF RIGID PACKAGING TO MEASURE INTERNAL OXYGEN CONCENTRATION WITH AN OPTICAL OXYGEN ANALYZER

(71) Applicant: Mocon, Inc., Minneapolis, MN (US)

(72) Inventor: John Eastman, Rogers, MN (US)

(73) Assignee: Mocon, Inc., Minneapolis, MN (US)

( * ) Notice: Subject to any disclaimer, the term of this patent is extended or adjusted under 35 U.S.C. 154(b) by 256 days.

(21) Appl. No.: 15/295,205

(22) Filed: Oct. 17, 2016

(51) Int. Cl.
  *G01N 31/22* (2006.01)
  *G01N 33/00* (2006.01)
  *G01N 21/64* (2006.01)

(52) U.S. Cl.
  CPC ....... *G01N 31/225* (2013.01); *G01N 21/6428* (2013.01); *G01N 33/0036* (2013.01); *G01N 33/0062* (2013.01); *G01N 2021/6432* (2013.01)

(58) Field of Classification Search
  CPC ............ G01N 31/225; G01N 33/0036; G01N 33/0062; G01N 21/6428; G01N 2201/6432
  USPC ... 73/1.06, 23.2, 23.21, 23.27, 23.31, 23.32, 73/31.01, 31.05; 356/43–50, 244, 246, 356/436–442; 422/83; 250/361 C, 250/483.1–488.1; 362/44; 436/160, 436/127–138
  See application file for complete search history.

(56) References Cited

U.S. PATENT DOCUMENTS

| | | | |
|---|---|---|---|
| 3,138,937 A | 6/1964 | Parkinson et al. | |
| 4,281,536 A | 8/1981 | Kraft et al. | |
| 4,622,974 A | 11/1986 | Coleman et al. | |
| 4,784,811 A | 11/1988 | Hirschfeld | |
| 5,230,427 A | 7/1993 | Betts et al. | |
| 5,284,570 A | 2/1994 | Savage et al. | |
| 5,328,823 A | 7/1994 | Spencer et al. | |
| 5,333,609 A | 8/1994 | Beningham et al. | |
| 6,258,063 B1 | 7/2001 | Haar et al. | |

(Continued)

FOREIGN PATENT DOCUMENTS

| CA | 2600566663 A1 | 9/2006 |
|---|---|---|
| EP | 0520443 B1 | 1/1997 |

(Continued)

OTHER PUBLICATIONS

Multisorb Technologies, FRESHPAX, Oxygen Absorbing Packets and Strips, 2009.

(Continued)

*Primary Examiner* — Robert R Raevis
(74) *Attorney, Agent, or Firm* — Sherrill Law Offices, PLLC

(57) ABSTRACT

An assembly and method of using the assembly. The assembly is operable when assembled as a benchtop instrument for sealed penetration of an oxygen sensitive luminescent sensor into sensible communication with an enclosed space of a sealed rigid package to measure oxygen concentration therein, and operable when disassembled as a handheld instrument for sealed penetration of the oxygen sensitive luminescent sensor into sensible communication with an enclosed space of a flexible package to measure oxygen concentration therein. The assembly includes a mechanical punch press equipped with a longitudinally reciprocable fixture equipped with a hollow piercing member, and an oxygen analyzer releasably attachable to the fixture.

10 Claims, 11 Drawing Sheets

(56) References Cited

U.S. PATENT DOCUMENTS

| | | |
|---|---|---|
| 6,328,932 B1 | 12/2001 | Carter et al. |
| 8,173,438 B1 | 5/2012 | Putman et al. |
| 9,057,687 B2* | 6/2015 | Eastman .............. G01N 21/278 |
| 9,316,554 B1* | 4/2016 | Eastman .............. G01L 19/0092 |
| 9,568,400 B2* | 2/2017 | Dykes, Jr. ............. G01N 1/2226 |
| 2003/0221477 A1 | 12/2003 | Prirskalla et al. |
| 2003/0235513 A1 | 12/2003 | Asai et al. |
| 2005/0113658 A1 | 5/2005 | Jacobson et al. |
| 2006/0144811 A1 | 7/2006 | Cheng |
| 2007/0227270 A1* | 10/2007 | Mennenga ................ A61J 1/20 73/863.85 |
| 2007/0243618 A1* | 10/2007 | Hatchett ................. G01M 3/38 436/1 |
| 2008/0072992 A1 | 3/2008 | Baleriaux et al. |
| 2008/0146902 A1 | 6/2008 | Hacker et al. |
| 2009/0075321 A1 | 3/2009 | Obeid et al. |
| 2009/0084156 A1 | 4/2009 | Matsuda et al. |
| 2009/0326344 A1 | 12/2009 | Meyer |
| 2010/0116017 A1 | 5/2010 | Mayer et al. |
| 2010/0173046 A1* | 7/2010 | Lisa ....................... A21D 10/02 426/107 |
| 2011/0223678 A1 | 9/2011 | Ascheman et al. |
| 2012/0129268 A1 | 5/2012 | Mayer |
| 2013/0251593 A1* | 9/2013 | Eastman .............. G01N 21/643 422/82.08 |
| 2013/0276508 A1* | 10/2013 | Eastman .............. G01N 21/278 73/1.06 |

FOREIGN PATENT DOCUMENTS

| | | |
|---|---|---|
| EP | 1887344 A1 | 2/2008 |
| EP | 2336753 A2 | 6/2011 |
| WO | 1992019150 | 11/1992 |
| WO | 2006095191 A1 | 9/2006 |

OTHER PUBLICATIONS

Papkovsky, Dmitri et al., "Biosensors on the basis of luminescent oxygen sensor: the use of microporous light-scattering support materials", Biochemestry Department, National University of Ireland, Cork, Elsevier, 1998. pp. 137-145.

* cited by examiner

INSTRUMENT AND METHOD FOR SEALED PENETRATION OF RIGID PACKAGING TO MEASURE INTERNAL OXYGEN CONCENTRATION WITH AN OPTICAL OXYGEN ANALYZER

BACKGROUND

Photoluminescent sensors or probes are a widely employed method of measuring analyte concentration, typically oxygen, within a defined space, typically an enclosed space such as the headspace of a package or container. See, for example United States Published Patent Applications 2009/0029402, 2008/8242870, 2008/215254, 2008/199360, 2008/190172, 2008/148817, 2008/146460, 2008/117418, 2008/0051646, and 2006/0002822, and U.S. Pat. Nos. 7,569,395, 7,534,615, 7,368,153, 7,138,270, 6,689,438, 5,718,842, 4,810,655, and 4,476,870.

Briefly, analyte concentration within a package or container can be measured by placing an analyte-sensitive photoluminescent sensor within the package or container, allowing the sensor to equilibrate within the package or container, exciting the sensor with radiant energy, and measuring the extent to which radiant energy emitted by the excited sensor is quenched by the presence of the target analyte. Such optical sensors are available from a number of suppliers, including PreSens Precision Sensing, GmbH of Regensburg, Germany, Oxysense of Dallas, Tex., United States, and Luxcel Biosciences, Ltd of Cork, Ireland.

In order to permit impromptu testing of a defined space, the photoluminescent sensor can be provided as a coating on the distal tip of a fiber optic filament which is then positioned within the lumen of a needle. An example of such a fiber optic sensing instrument for use in measuring the concentration of oxygen within living tissue is described in U.S. Pat. No. 8,383,047, the entire disclosure of which is hereby incorporated by reference. Another example of such a fiber optic sensing instrument for use in measuring the concentration of oxygen within the headspace of flexible packages is described in U.S. Pat. No. 9,316,554, the entire disclosure of which is hereby incorporated by reference.

Fiber optic sensing instruments can also be used for impromptu measurement of the total oxygen content in a rigid package containing a liquid, such as standard metal containers, by reciprocally mounting the fiber optic sensing needle within a hollow piercing member, piercing the metal container with the piercing member, extending the fiber optic sensing needle past the distal end of the piercing member and into fluid communication with the headspace of the container for measuring gaseous oxygen concentration, and then further extending the fiber optic sensing needle into fluid communication with the fluid contents of the container for measuring the concentration of dissolved oxygen in the fluid contents of the container, such as described in European Patent Application EP 1887344.

The instrument described in U.S. Pat. No. 9,316,554, while effective as a portable instrument for measuring oxygen concentration in flexible packaging, is not suited and essentially incapable of measuring the oxygen concentration in rigid packaging as it cannot penetrate the packaging. The oxygen concentration in rigid packaging can be measured with the instrument described in EP 1887344, but this instrument is not portable and is not well suited for measuring the oxygen concentration in flexible packaging as the instrument will frequently cause the flexible packaging to burst. Unfortunately, many manufacturers need to test the oxygen concentration of both rigid packages and flexible packages, and due to the use limitations of the available testing instruments are required to purchase separate testing instruments, one for each type of packaging.

Hence, a need exists for a fiber optic sensing instrument suitable for use in measuring the concentration of oxygen within the headspace of both rigid and flexible packages.

SUMMARY OF THE INVENTION

A first aspect of the invention is an assembly operable when assembled as a benchtop instrument for sealed penetration of the oxygen sensitive luminescent sensor into sensible communication with an enclosed space of a sealed rigid package, and operable when disassembled as a handheld instrument for sealed penetration of the oxygen sensitive luminescent sensor into sensible communication with an enclosed space of a flexible package.

The assembly includes (—) a first component comprising a mechanical punch press equipped with a longitudinally reciprocable fixture having a sharp-tipped, rigid, lumen defining, hollow piercing member extending in a first longitudinal direction from the fixture, and a longitudinal bore extending completely through the fixture and into fluid communication with the lumen of the piercing member, and (—) a second component comprising an oxygen analyzer having an oxygen sensitive luminescent sensor retained within a rigid, lumen defining, hollow, side-port needle proximate a distal end of the needle, with the fixture and the oxygen analyzer configured and arranged relative to one another for sealed, detachable, mounting of the oxygen analyzer onto the fixture with the needle on the oxygen analyzer extending into the bore of the fixture with the distal tip of the needle positioned within the lumen of the piercing member.

A second aspect of the invention is a method of serially measuring oxygen concentration inside each of a sealed rigid package and a sealed flexible package using an assembly in accordance with the first aspect of the invention. The method includes the steps of measuring oxygen concentration inside a sealed rigid package with the components assembled, and measuring oxygen concentration inside a sealed flexible package with the components disassembled. The step of measuring oxygen concentration inside a sealed rigid package with the assembled assembly includes the steps of (i) piercing the rigid package with the piercing member by actuation of the mechanical punch press so as to cause the piercing member to penetrate into the sealed rigid package with the fixture sealingly engaging the sealed rigid package, (ii) allowing the oxygen concentration in sensing communication with the oxygen sensitive luminescent sensor to equilibrate with the oxygen concentration in the sealed rigid package, (iii) activating the oxygen analyzer whereby the oxygen analyzer optically interrogates the oxygen sensitive luminescent sensor to obtain a value representative of the partial pressure of oxygen in the sealed rigid package, (iv) converting the obtained value to an oxygen concentration based upon a known conversion algorithm, and (v) visually reporting the oxygen concentration. The step of measuring oxygen concentration inside a sealed flexible package with a disassembled assembly includes the steps of (i) piercing the flexible package with the needle of the oxygen analyzer, (ii) allowing the oxygen concentration in sensing communication with the oxygen sensitive luminescent sensor to equilibrate with the oxygen concentration in the sealed flexible package, (iii) activating the oxygen analyzer whereby the oxygen analyzer optically interrogates the oxygen sensitive luminescent sensor to obtain a value representative of the partial pressure of oxygen in the sealed flexible package, (iv) converting the obtained value to an oxygen concentration based upon a known conversion algorithm, and (v) visually reporting the oxygen concentration.

The second aspect of the invention may further include the step of adhering a septum to the exterior of the rigid package, with subsequent piercing of the rigid package occurring through the adhered septum, and/or adhering a septum to the exterior of the flexible package, with subsequent piercing of the flexible package occurring through the adhered septum.

DETAILED DESCRIPTION OF A PREFERRED EMBODIMENT

Definitions

As used herein, including the claims, the phrase "rigid packaging" means packaging that both retains its shape when the product is not present and defies low velocity hand puncture by a round point 17 gauge industrial metal needle. Exemplary rigid packaging includes polyethylene laundry detergent bottles, polyurethane soda bottles, standard #2 cans, etc.

NOMENCLATURE

100 Analytical Instrument
200 Punch Press
210 Base of Punch Press
212 Adjustable Positioning Stops
219 Radial Slots in Base of Punch Press
220 Vertical Support Post
222 Rack
230 Punch Head
240 Release and Lock for Vertical Adjustment of Punch Head
250 Capstan Wheel for Leveraged Vertical Reciprocation of Punch Head
260 Fixture Clamp on Punch Head
262 Lock and Release for Fixture Clamp
300 Fixture
300a First or Upper External Surface of Fixture
300b Second or Lower External Surface of Fixture
309 Longitudinal Bore Through Fixture
310 Piercing Member
310b Distal Tip of Piercing Member
318 Lumen in Piercing Member
331 First or Upper O-ring Seal
332 Second or Lower O-ring Seal
400 Oxygen Analyzer
410a Collared Needle Subassembly of Instrument
410b Optical Block Subassembly of Instrument
410c Handle Portion of Instrument
420 Tube or Hollow Shank (Collectively Needle)
$420_1$ Proximal End of Needle
$420_2$ Distal End of Needle
$420_3$ Inner Surface of Needle
428 Ports in Needle
429 Lumen of Needle
$429_1$ Proximal End of Lumen
$429_2$ Distal End of Lumen
430 Collar
440 Thread Fitting
441 Outer O-ring
442 Inner O-ring
450 Fiber Optic Filament
$450_1$ Proximal End of Fiber Optic Filament
$450_2$ Distal End of Fiber Optic Filament
$450_4$ Outer Surface of Fiber Optic Filament
460 Void Volume Channel Sealing O-rings
468 Void Volume Channel
469 Branch Channel
470 Photoluminescent Oxygen-Partial-Pressure-Sensitive Sensor
480 Photoluminescence Detector
481 Source of Excitation Radiant Energy
490 Pressure Sensor
500 Microprocessor
510 Display
520 Activation Trigger
600 Septum
P Rigid Package
$P_1$ Enclosed Space of Rigid Package
S Flexible Package
$S_1$ Enclosed Space of Flexible Package

Construction

Figure 1:
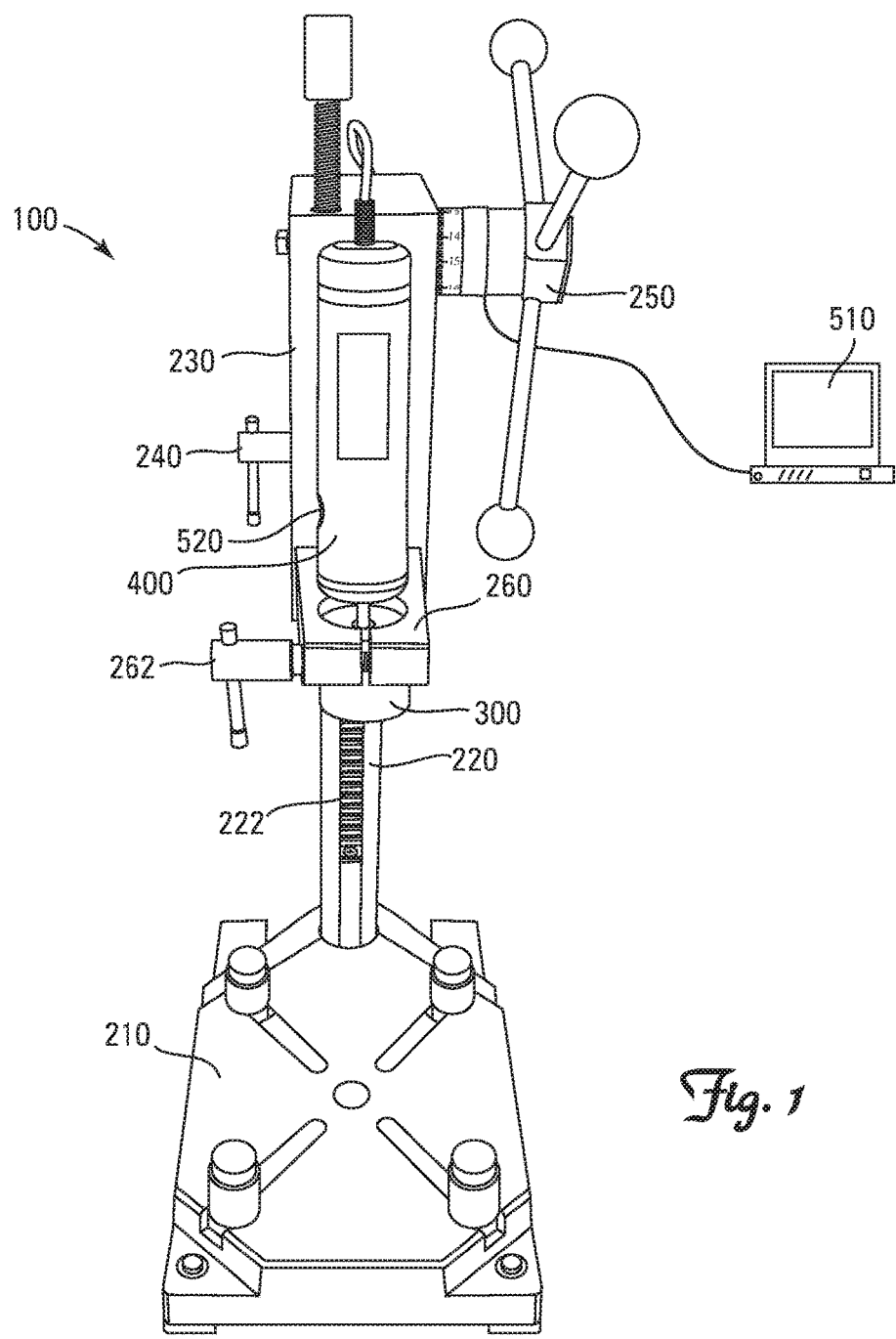
FIG. 1 is a front perspective view of one embodiment of the fully assembled invention.
Figure 2:
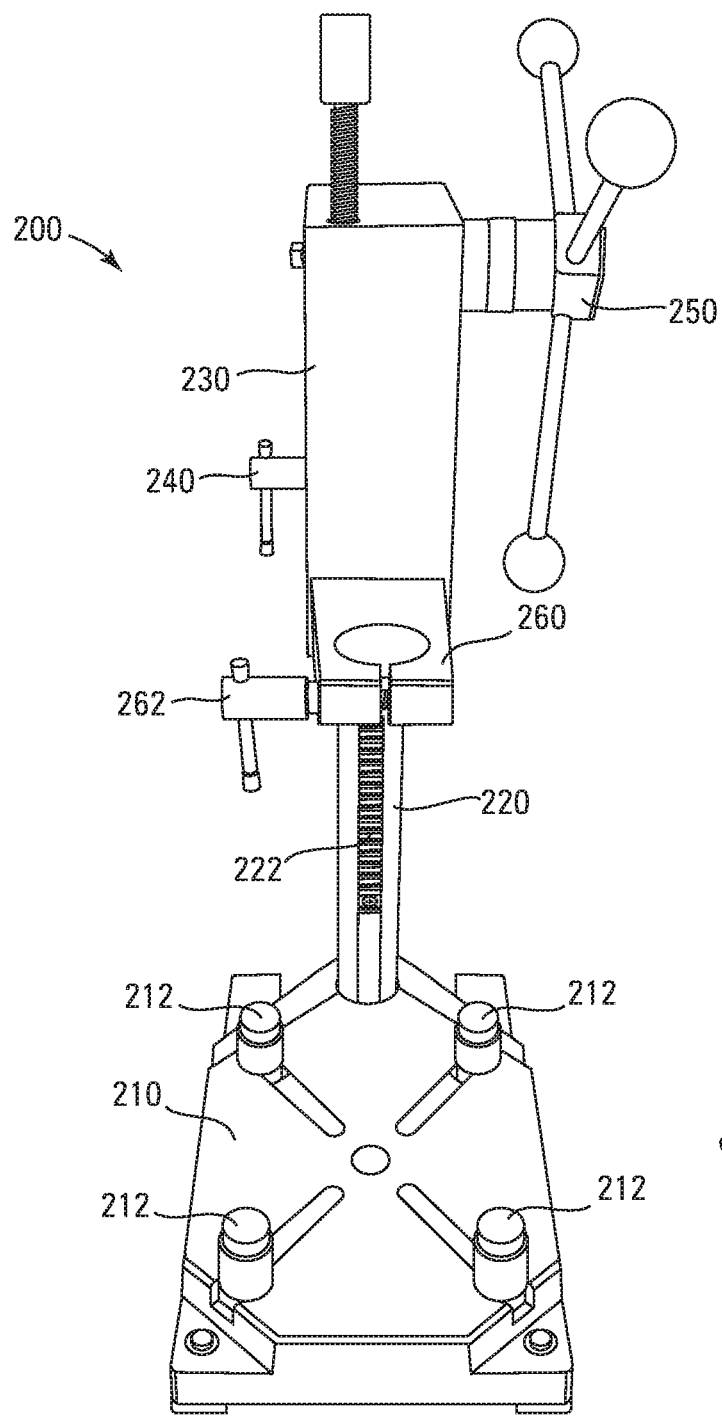
FIG. 2 is a front perspective view of the mechanical punch press component of the invention depicted in FIG. 1, sans fixture.
Figure 3:
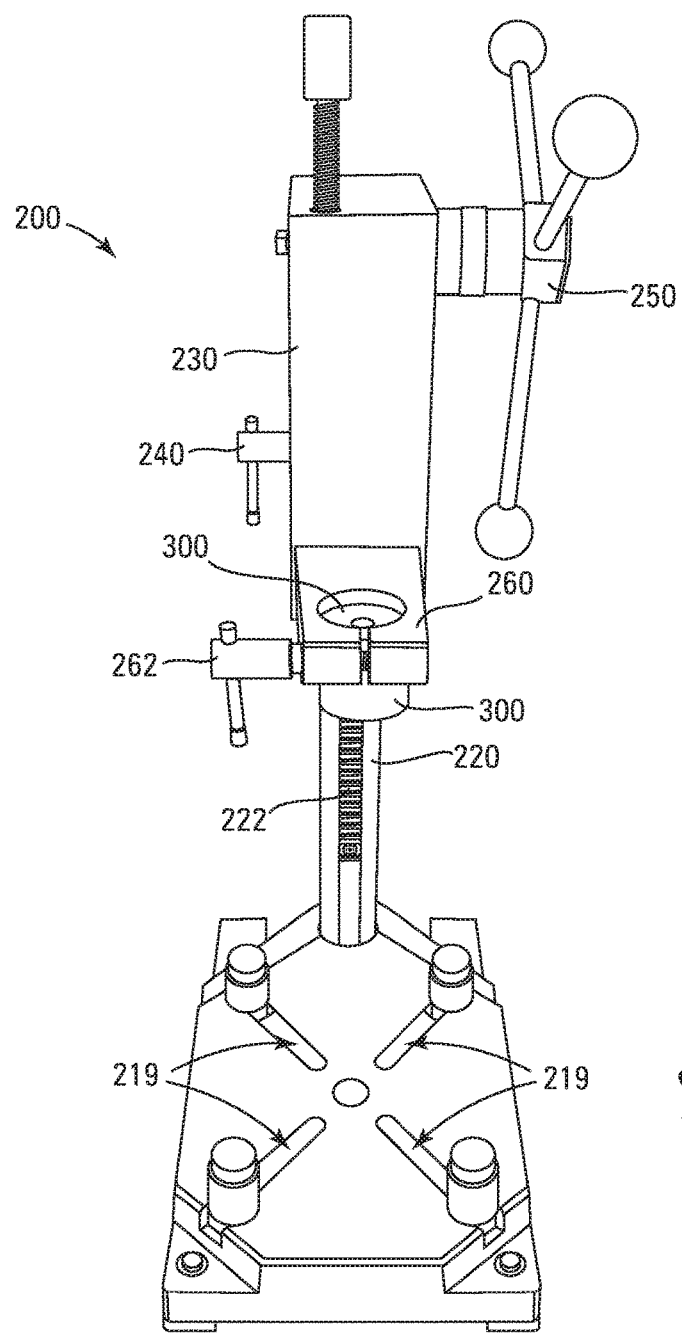
FIG. 3 is a front perspective view of the mechanical punch press component of the invention depicted in FIG. 2 with one embodiment of the fixture retained within the clamp of the mechanical punch press.
Figure 4:
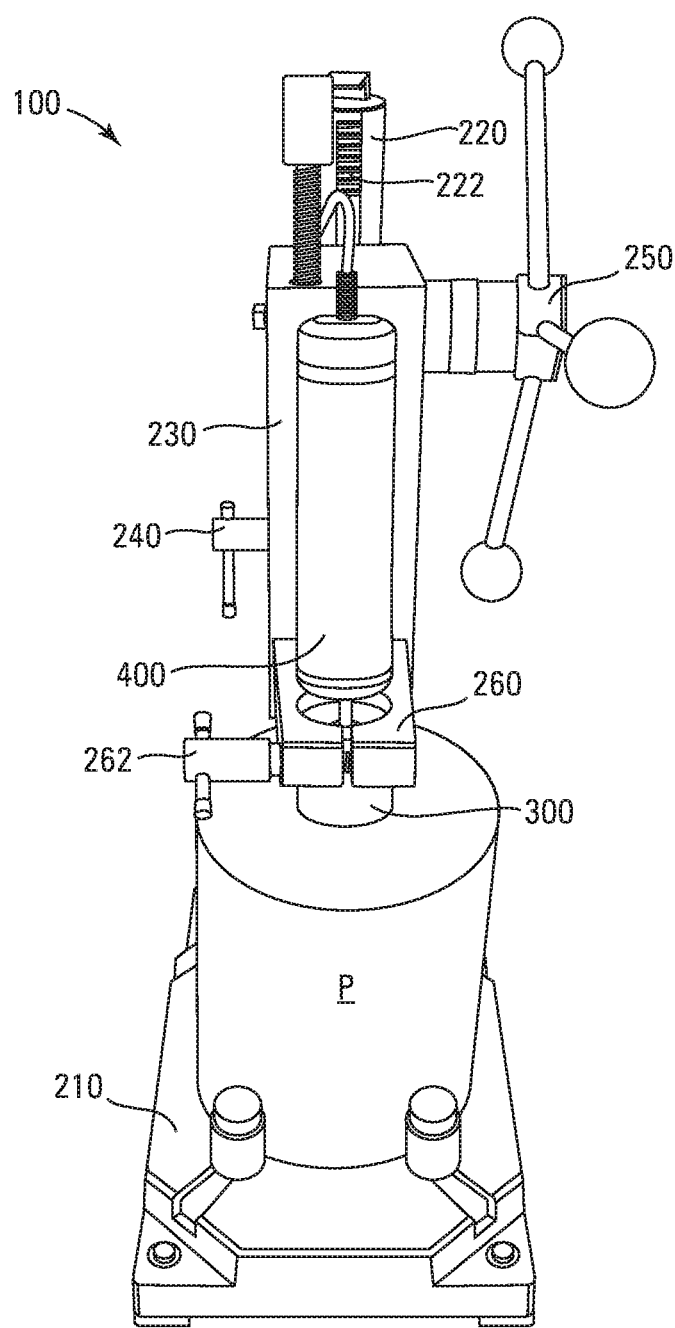
FIG. 4 is a front perspective view of the assembled invention depicted in FIG. 1 with a rigid package resting upon the base of the mechanical punch press.

Referring generally to FIG. 1, a first aspect of the invention is an assembly 100 operable when assembled as a benchtop instrument 100 for sealed penetration of an oxygen sensitive luminescent sensor 470 into sensible communication with an enclosed space $P_1$ of a sealed rigid package P, and operable when disassembled as a handheld instrument 400 for sealed penetration of the oxygen sensitive luminescent sensor 470 into sensible communication with an enclosed space $S_1$ of a flexible package S.

The assembly 100 includes a first component comprising a mechanical punch press 200 equipped with a longitudinally reciprocable fixture 300, and a second component comprising an oxygen analyzer 400.

Mechanical Punch Press

Referring to FIGS. 1-5, the mechanical punch press 200 has a support post 220 extending vertically upward from a base 210. The base 210 is preferably equipped with four positioning stops 212 adjustable along radial slots 219 in the base 210 for facilitating stable centering of variably sized rigid packages P upon the base 210. A punch head 230 is supported upon the support post 220 above the base 210. The punch head 230 is vertically translatable along a vertical rack 222 on the support post 220 by manual actuation of a capstan wheel 250.

The mechanical punch press 200 preferably includes a release and lock 240 for allowing vertical adjustment of the punch head 230 upon the support post 220.

Referring to FIGS. 1 and 3-5, the fixture 300 is mounted on the punch head 230 with a piercing member 310 projecting longitudinally downward from the second or lower external surface 300b of the fixture 300 towards the base 210. The fixture 300 may be permanently or releasably secured to the punch head 230, with a preference for releasable attachment via a fixture clamp 260 equipped with a lock and release mechanism 262.

Figure 6:
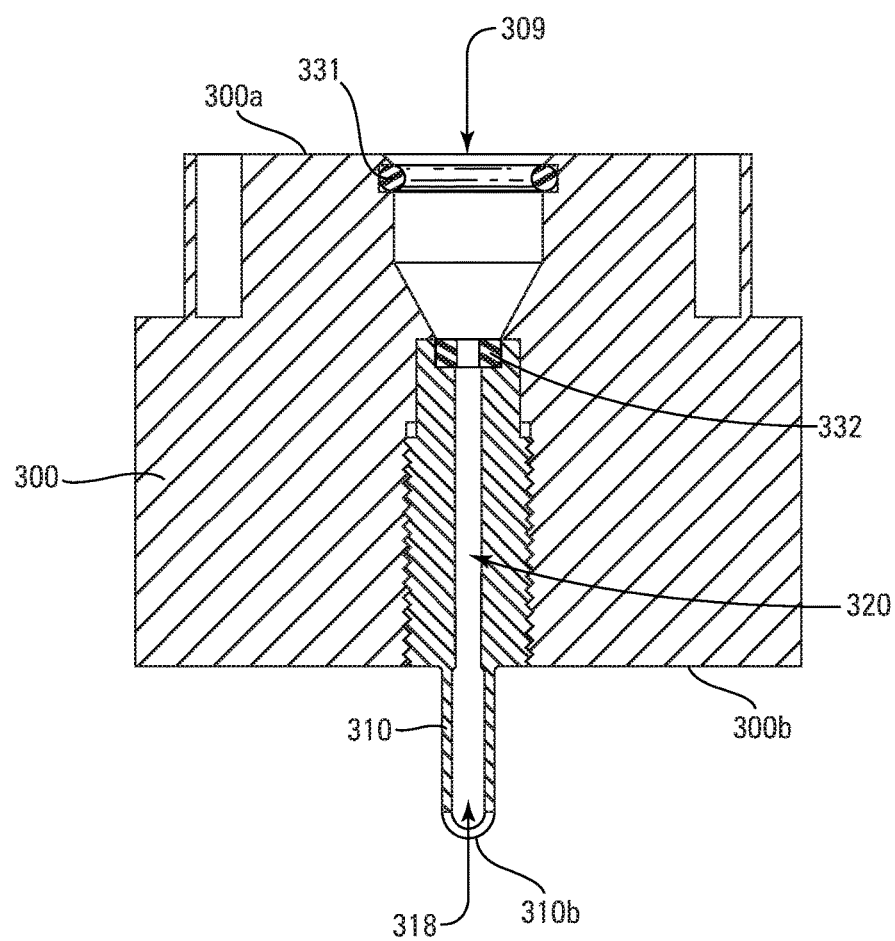
FIG. 6 is a cross-sectional view of the fixture depicted in FIGS. 1 and 3-5.
Figure 7:
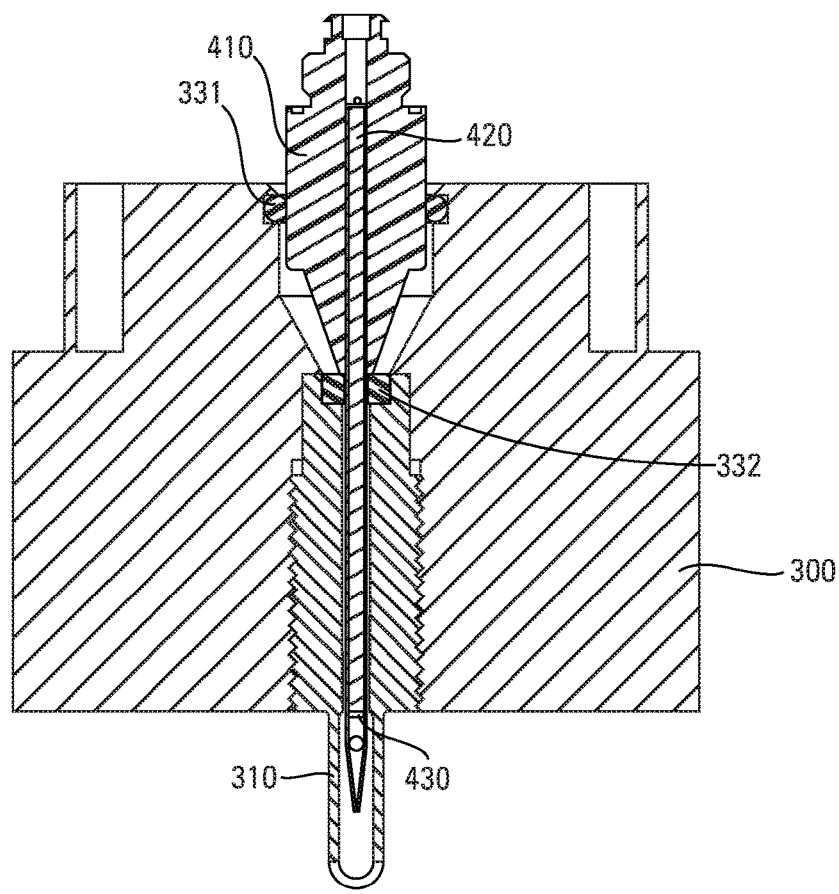
FIG. 7 is a cross-sectional view of the fixture and portion of the oxygen analyzer engaged therein depicted in FIGS. 1, 4 and 5.
Figure 8:
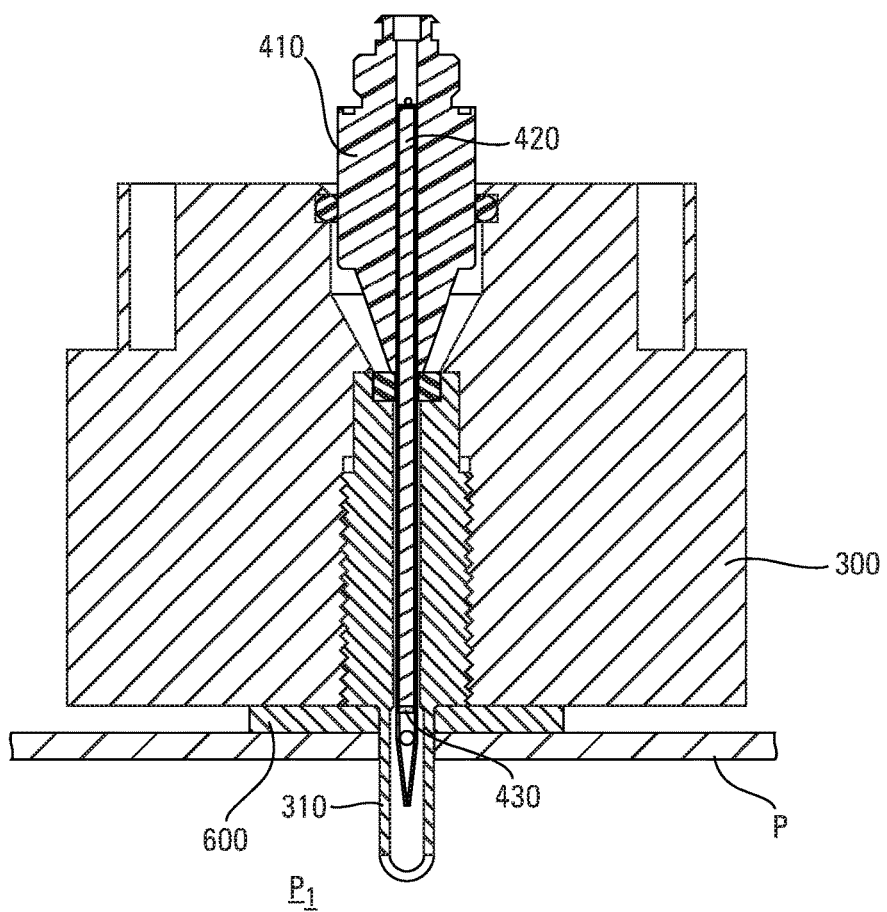
FIG. 8 is an enlarged cross-sectional view of the fixture and portion of the oxygen analyzer engaged therein depicted in FIGS. 1, 4 and 5 after piercing a rigid package.

Referring to FIGS. 6-8, the piercing member 310 is a rigid projection having an open, sharp distal tip 310b and an internal lumen 318 extending the full longitudinal length of the piercing member 310. A longitudinal bore 309 extends completely through the fixture 300 from the first or upper external surface 300a to the second or lower external surface 300b and into fluid communication with the lumen 318 in the piercing member 310.

The bore 309 through the fixture 300 is preferably equipped with upper 331 and lower 332 O-rings for sealingly engaging an oxygen analyzer 400 releasably mounted upon the fixture 300 with the needle 420 of the oxygen analyzer 400 projecting through the bore 309 and into the lumen 318 of the piercing member 310.

Oxygen Analyzer

An exemplary oxygen analyzer 400 suitable for use in the present assembly 100 is described in U.S. Pat. No. 9,316,554, the entire disclosure of which is hereby incorporated by reference.

Referring generally to FIGS. 7-11, the oxygen analyzer 400 is a photoluminescent fiber optic oxygen-sensing instrument employing a photoluminescent oxygen-partial-pressure-sensitive sensor 470 located within the lumen 429 of a needle 420 proximate the distal end $420_2$ of the needle 420, and at least one fiber optic filament 450, preferably a single unjacketed fiber, that extends axially along the length of the lumen 429.

Figure 9:
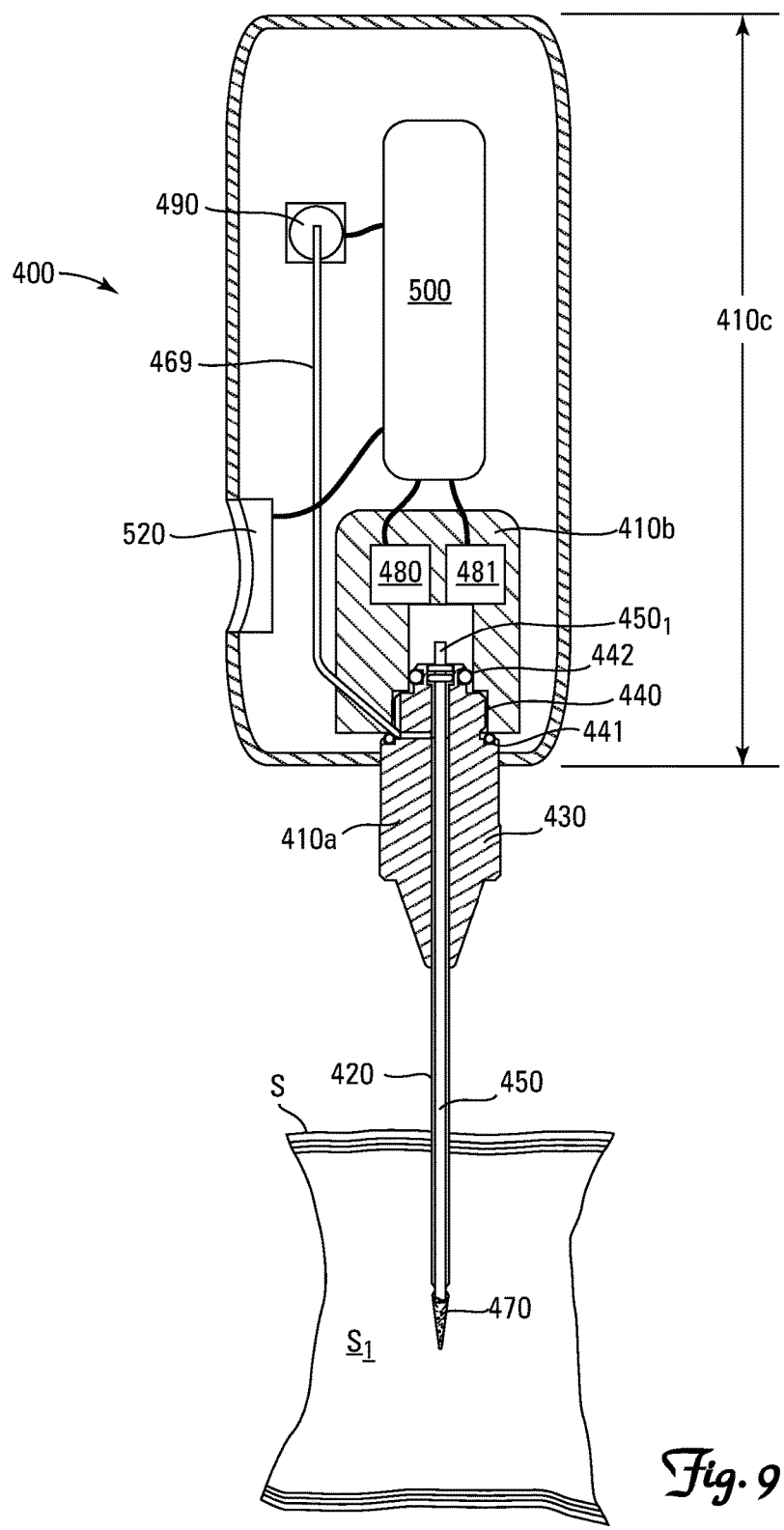
FIG. 9 is a cross-sectional view of the oxygen analyzer component of the invention disassembled from the mechanical punch press component, with the needle of the oxygen analyzer piercing a flexible package.
Figure 10:
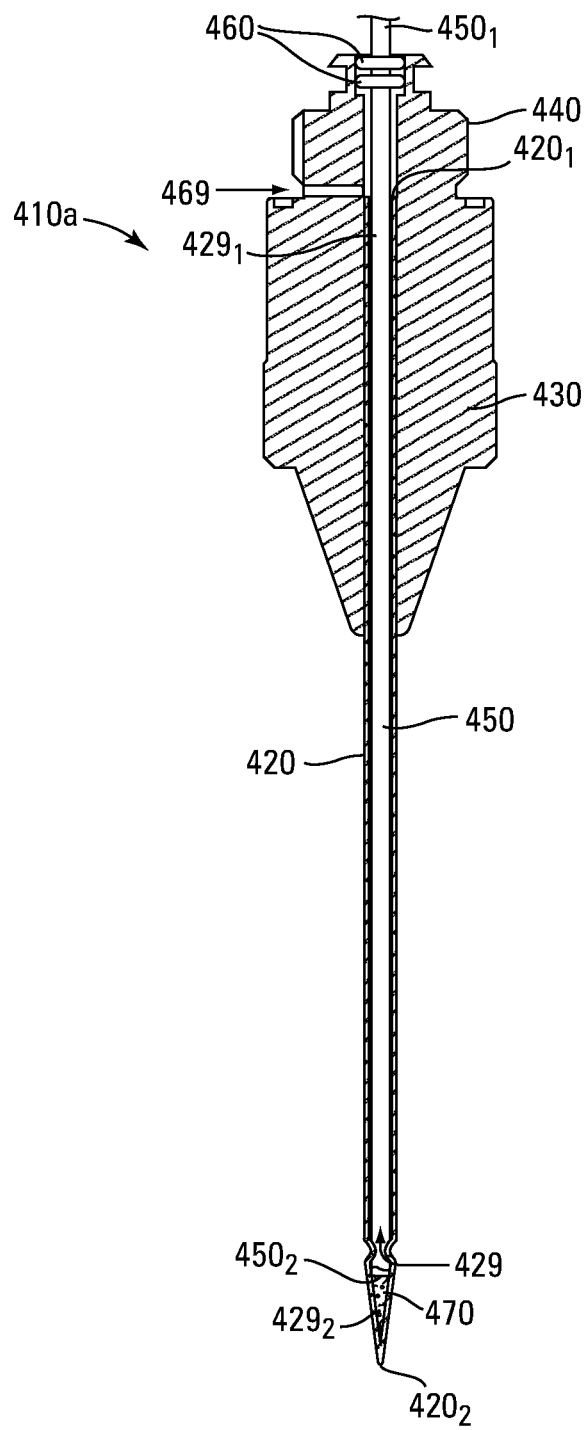
FIG. 10 is an enlarged cross-sectional side view of the needle and collar portions of the oxygen analyzer component of the invention depicted in FIG. 9.
Figure 11:
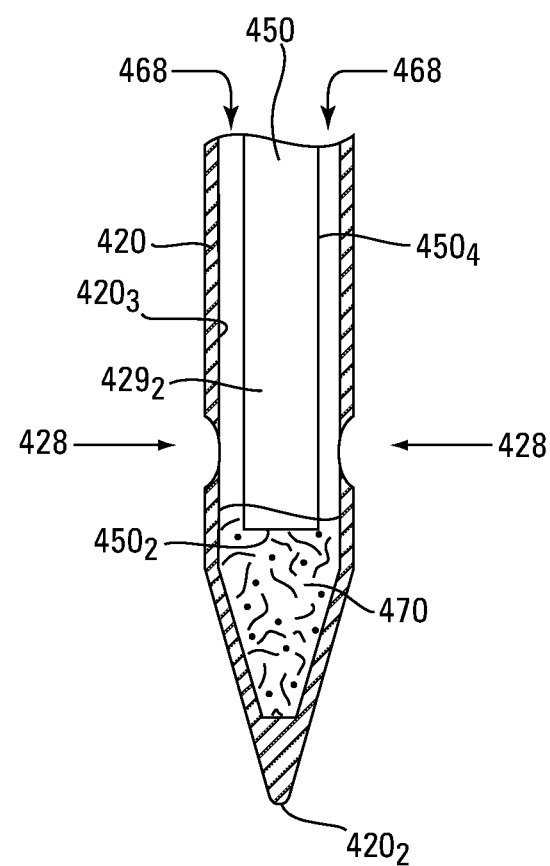
FIG. 11 is an enlarged cross-sectional side view of the distal end portion of the needle portion of the oxygen analyzer component of the invention depicted in FIG. 9.

Referring to FIGS. 9-11, the oxygen analyzer 400 can include a pressure compensation feature, by providing a void volume channel 468 that extends along the length of the lumen 429 between the inner surface $420_3$ of the needle 420 and the outer surface $450_4$ of the at least one fiber optic filament 450, and a pressure sensor 490 in pressure communication with the same fluid communicating with the photoluminescent oxygen-partial-pressure-sensitive sensor 470 via the void volume channel 468. The pressure sensor 490 permits pressure compensation of oxygen-concentration values calculated from oxygen-partial-pressure readings taken from the photoluminescent oxygen-partial-pressure-sensitive sensor 470.

Referring generally to FIGS. 9-11, the needle 420 has a longitudinal lumen 429 with at least one port 428 proximate the distal tip $420_2$ of the needle 420. The port 428 is preferably a lateral side port 428 with the needle 420 preferably having at least two diametrically opposed lateral side ports 428. The needle 420 can be a sharp tipped or blunt tipped needle 420 and preferably has a nominal inner diameter (i.e., lumen 429) of between 1.0 to 3.5 mm.

The proximal end $420_1$ of the needle 420 is preferably attached to a collar 430 via brazing, soldering or gluing. The collar 430 is preferably fitted with a pair of O-rings 441 and 442 and is suitable for sealed threadable attachment to the optical block subassembly 410b of the instrument 400 via a thread fitting 440.

The at least one fiber optic filament 450 extends axially along the length of the lumen 429 from a proximal end $450_1$ proximate the proximal end $429_1$ of the lumen 429 to a distal end $450_2$ proximate the distal end $429_2$ of the lumen 429 and in sensing communication with the photoluminescent oxygen-partial-pressure-sensitive sensor 470.

When the oxygen analyzer 400 includes the pressure compensation feature, the outside diameter of the at least one fiber optic filament 450 is preferably smaller than the inside diameter of the needle 420 so as to form a void volume channel 468 along the length of the lumen 429. As a result of the inherent axial curvature and flexibility of typical fiber optic filaments 450, the void volume channel 468 may be an amorphous channel. The proximal end $450_1$ of the fiber optic filament 450 is preferably sealingly engaged to the inner surface $420_3$ of the needle 420 or the inner surface (not separately numbered) of the bore (not separately numbered) of the collar 430 by a suitable sealing means such as a sealant (e.g., epoxy) or one or more O-rings 460, to secure the at least one fiber optic filament 450 within the lumen 429 and prevent the atmosphere located outside a package P or S being tested from reaching and contaminating the photoluminescent oxygen-sensitive sensor 470 and/or the pressure sensor 490 through the annular interface between the inner surface $420_3$ of the needle 420 and the outer surface $450_4$ of the fiber optic filament 450.

The photoluminescent oxygen-sensitive sensor 470 is located within the lumen 429 between the distal tip $450_2$ of the at least one fiber optic filament 450 and the distal tip $420_2$ of the needle 420, and is in sensing fluid communication with the external environment, such as the enclosed space $P_1$ or $S_1$ of a rigid package P or a flexible package S respectively, through the at least one port 428 in the needle 420.

The photoluminescent oxygen-partial-pressure-sensitive sensor 470 can be selected from the numerous commercially available types of such sensors. Generally, such sensors comprise a carrier substrate coated with an oxygen-sensitive photoluminescent dye, often with the oxygen-sensitive photoluminescent dye embedded within an oxygen-permeable polymer matrix.

When employed, the carrier substrate may be selected from any material possessing sufficient structural integrity to physically support the oxygen-sensitive photoluminescent dye and capable of withstanding extended exposure to the environment into which the sensor 470 is to be used (e.g., high humidity, low humidity, submerged in water, submerged in an acidic solution, etc). Materials suitable for use as the carrier substrate, dependent of course upon the environment to which the sensor 470 is to be exposed during normal usage, include specifically but not exclusively, cellulosics such as paper, wax paper, cardstock, cardboard, wood and wood laminates; plastics such as polyethylene, polypropylene and polyethylene terephthalate; metals such as aluminum sheets, aluminum foil, steel and tin; woven and unwoven fabrics; glass; and various combinations and composites thereof such a Mylar.

The oxygen-sensitive photoluminescent dye may be selected from any of the well-known oxygen-sensitive photoluminescent dyes. One of routine skill in the art is capable of selecting a suitable dye based upon the intended use of the oxygen analyzer 400. For example, a nonexhaustive list of suitable oxygen-sensitive photoluminescent dyes includes specifically, but not exclusively, ruthenium(II)-bipyridyl and ruthenium(II)-diphenylphenanothroline complexes, porphyrin-ketones such as platinum(II)-octaethylporphine-ketone, platinum(II)-porphyrin such as platinum(II)-tetrakis(pentafluorophenyl)porphine, palladium(II)-porphyrin such as palladium(II)-tetrakis(pentafluorophenyl)porphine, phosphorescent metallocomplexes of tetrabenzoporphyrins, chlorins, azaporphyrins, and long-decay luminescent complexes of iridium(III) or osmium(II).

Typically, the oxygen-sensitive photoluminescent dye is compounded with a suitable oxygen-permeable polymer matrix. Again, one of routine skill in the art is capable of selecting a suitable oxygen-permeable polymer matrix based upon the intended use of the oxygen analyzer 400. For example, a nonexhaustive list of suitable polymers for use as an oxygen-permeable polymer matrix includes specifically, but not exclusively, polystyrene, polycarbonate, polysulfone, polyvinyl chloride and some co-polymers.

Referring to FIG. 9, the proximal end 450$_1$ of the at least one fiber optic filament 450 is in optical communication with a photoluminescence detector 480 for transmitting excitation radiant energy from a source of excitation radiant energy 481 to the photoluminescent oxygen-partial-pressure-sensitive sensor 470, and thereafter transmitting radiant energy emitted by the excited sensor 470 back to the photoluminescence detector 480 where a $P_{OXYGEN}$ electrical signal, representative of the oxygen-partial-pressure of a fluid in fluid communication with the sensor 470 is generated. The radiant energy emitted by the excited sensor 470 can be measured in terms of intensity and/or lifetime (rate of decay, phase shift or anisotropy), with measurement of lifetime generally preferred as a more accurate and reliable measurement technique when seeking to establish oxygen concentration via measurement of the extent to which an oxygen-sensitive photoluminescent dye has been quenched by the oxygen.

Referring to FIGS. 9 and 11, when the oxygen analyzer 400 includes the pressure compensation feature, the void volume channel 468 can be placed in pressure communication with a pressure sensor 490 for communicating sample-fluid total pressure (i.e., the total pressure of the fluid in sensing fluid communication with the photoluminescent oxygen-partial-pressure-sensitive sensor 470) to the pressure sensor 490, whereby the pressure sensor 490 can generate a $P_{SAMPLE\ TOTAL}$ electronic signal representative of the sample-fluid total-pressure in fluid communication with the sensor 470. A diaphragm (not shown) may be interposed between the pressure sensor 490 and a sample-fluid in communication with the sensor 470, but is generally unnecessary. Hence, the pressure sensor 490 may typically be in direct fluid communication with the sample-fluid communicating with the sensor 470. Referring to FIG. 10, in order to facilitate placement of the pressure sensor 490 at a convenient location in the handle of the instrument 400, a branch channel 469 may be provided to fluidly connect a remotely located pressure sensor 490 with the void volume channel 468.

A user actuated trigger 520 is provided for initiating the taking of a $P_{OXYGEN}$ reading by the photoluminescence detector 480, or when the pressure compensation feature is employed temporally paired readings of $P_{SAMPLE\ TOTAL}$ and $P_{OXYGEN}$ by the pressure sensor 490 and the photoluminescence detector 480, respectively. The $P_{SAMPLE\ TOTAL}$ and $P_{OXYGEN}$ readings may be taken in serial or parallel fashion, but are preferably taken simultaneously.

$P_{OXYGEN}$ readings are transmitted from the photoluminescence detector 480 to a microprocessor 500 which converts the obtained value to an oxygen concentration based upon a known conversion algorithm, and displays the oxygen concentration on an electronic display 510. The microprocessor 500 is preferably integrated into the handle of the instrument 400 while the display 510 is preferably located remotely from the instrument 400, receiving values from the microprocessor 500 via wired or wireless transmission from the microprocessor 500.

When the oxygen analyzer 400 includes the pressure compensation feature, temporally paired readings of $P_{SAMPLE\ TOTAL}$ and $P_{OXYGEN}$ are transmitted from the pressure sensor 490 and the photoluminescence detector 480, respectively, to a microprocessor 500 programmed to calculate an oxygen concentration (OXYGEN %) from these temporally paired electrical signals based at least in part upon the algorithm set forth below, and display the calculated oxygen concentration on an electronic display 510.

$$OXYGEN\ \% = (P_{CAL\ TOTAL}/P_{SAMPLE\ TOTAL})(P_{OXYGEN})$$

Wherein $P_{CAL\ TOTAL}$ is the total pressure of the gas sample used to calibrate the oxygen analyzer 400 as measured by the pressure sensor 490 during calibration.

The microprocessor 500 and display 510 may be located remotely from the instrument 400 and wired or wirelessly communicate with the pressure sensor 490 and the photoluminescence detector 480, but are preferably integrated into the handle of the instrument 400.

Use

The oxygen analyzer 400 can be used to quickly, easily, accurately and reliably measure oxygen concentration within the enclosed space $P_1$ of a rigid package P when combined with the mechanical punch press 200, and measure oxygen concentration within the enclosed space $S_1$ of a flexible package S when detached from the mechanical punch press 200. Accuracy of measurements can be ensured even though the enclosed space $P_1$ or $S_1$ may have a total pressure ($P_{SAMPLE\ TOTAL}$) which differs substantially from surrounding atmospheric pressure by providing the oxygen analyzer 400 with the pressure compensation feature.

Briefly, the oxygen analyzer 400 can be used to measure oxygen concentration within the enclosed space $P_1$ of a rigid package P or the enclosed space $S_1$ of a flexible package S by (A) placing the distal end portion 420$_2$ of the needle 420 into fluid communication with the enclosed space $P_1$ of a rigid package P or the enclosed space $S_1$ of a flexible package S to be tested, whereby both the oxygen-partial-pressure-sensitive photoluminescent sensor 470 and the pressure sensor 490 on the instrument 400 are placed into sensible communication with the enclosed space $P_1$ or $S_1$, (B) allowing the concentration of oxygen in sensible communication with the photoluminescent sensor 470 to equilibrate with the oxygen concentration within the enclosed space $P_1$ or $S_1$, (C) allowing the pressure in sensible communication with the pressure sensor 490 to equilibrate with the pressure of the enclosed space $P_1$ or $S_1$, and (D) ascertaining an oxygen concentration within the enclosed space $P_1$ or $S_1$ by: (i) measuring the total pressure of the enclosed space $P_1$ or $S_1$ with the equilibriated pressure sensor 490, (ii) exposing the equilibriated photoluminescent sensor 470 to excitation radiation, (iii) measuring radiation emitted by the excited photoluminescent sensor 470, and (iv) converting the measured emission to an oxygen concentration based upon a known pressure compensated conversion algorithm that employs the value of the measured total pressure ($P_{SAMPLE\ TOTAL}$) of the enclosed space $P_1$ or $S_1$ to pressure correct the converted measured emission.

When the oxygen analyzer 400 is used to measure oxygen concentration within the enclosed space $P_1$ of a rigid package P, the distal end portion 420$_2$ of the needle 420 on the oxygen analyzer 400 is placed into fluid communication with the enclosed space $P_1$ of the rigid package P by first sealingly mounting the oxygen analyzer 400 to the fixture 300 on the mechanical punch press 200, with the needle 420 on the oxygen analyzer 400 extending into the bore 309 of the fixture 300 with the distal tip 420$_2$ of the needle 420 positioned within the lumen 318 of the piercing member 310. The rigid package P is then placed upon the base 210 of the mechanical punch press 200 and the capstan wheel 250 rotated so as to lower the entire fixture 300 including the piercing member 310 downward towards the rigid package P, until the piercing member 310 is forced against and punctures through the top of the rigid package P and the lower external surface 300b of the fixture 300 sealingly engages against the top of the rigid package P.

When the oxygen analyzer 400 is used to measure oxygen concentration within the enclosed space $S_1$ of a flexible package S, the distal end portion 420$_2$ of the needle 420 on the oxygen analyzer 400 is placed into fluid communication with the enclosed space $P_1$ of the rigid package P by first detaching the oxygen analyzer 400 from to the fixture 300 on the mechanical punch press 200. The detached portable oxygen analyzer 400 can then be transported to a testing location and the needle 420 of the oxygen analyzer 400 hand pressed against a flexible package S to be tested until the needle 420 pierces the package S.

The oxygen analyzer 400 can also be used to quickly, easily, accurately and reliably monitoring changes in oxygen concentration within the enclosed space $P_1$ of a rigid package P or the enclosed space $S_1$ of a flexible package S. Accuracy of measurements can be ensured even though the enclosed space $P_1$ or $S_1$ may have a total pressure ($P_{SAMPLE\ TOTAL}$) which differs substantially from surrounding atmospheric pressure by providing the oxygen analyzer 400 with the pressure compensation feature. Briefly, the oxygen analyzer 400 can be used to monitoring changes in oxygen concentration within the enclosed space $P_1$ of a rigid package P or the enclosed space $S_1$ of a flexible package S by (A) placing the distal end portion 420$_2$ of the needle 420 into fluid communication with the enclosed space $P_1$ of a rigid package P or the enclosed space $S_1$ of a flexible package S to be tested, whereby both the oxygen-partial-pressure-sensitive photoluminescent sensor 470 and the pressure sensor 490 on the instrument 400 are placed into sensible communication with the enclosed space $P_1$ or $S_1$, (B) allowing the concentration of oxygen in sensible communication with the photoluminescent sensor 470 to equilibrate with the oxygen concentration within the enclosed space $P_1$ or $S_1$, (C) allowing the pressure in sensible communication with the pressure sensor 490 to equilibrate with the pressure of the enclosed space $P_1$ or $S_1$, and (D) ascertaining an oxygen concentration within the enclosed space $P_1$ or $S_1$ by: ($\alpha$) coincidentally and repeatedly measuring the total pressure ($P_{SAMPLE\ TOTAL}$) of the enclosed space $P_1$ or $S_1$ with the equilibrated pressure sensor 490, and the partial pressure of oxygen ($P_{OXYGEN}$) in the enclosed space $P_1$ or $S_1$ with the equilibrated photoluminescent sensor 470, ((3) measuring passage of time ($\Delta t$) during the repeated coincidental measurements, and ($\gamma$) converting at least some of the coincidental measurements to an oxygen concentration (OXYGEN %) based upon a known pressure compensated conversion algorithm that employs the value of the measured total pressure ($P_{SAMPLE\ TOTAL}$) of the enclosed space $P_1$ or $S_1$, and (E) reporting at least one of ($\alpha$) at least two ascertained oxygen concentrations (OXYGEN %) and the time interval ($\Delta t$) between those reported concentrations, and ($\beta$) a rate of change in oxygen concentration within the enclosed space $P_1$ or $S_1$ calculated from data obtained in step (D).

Figure 5:
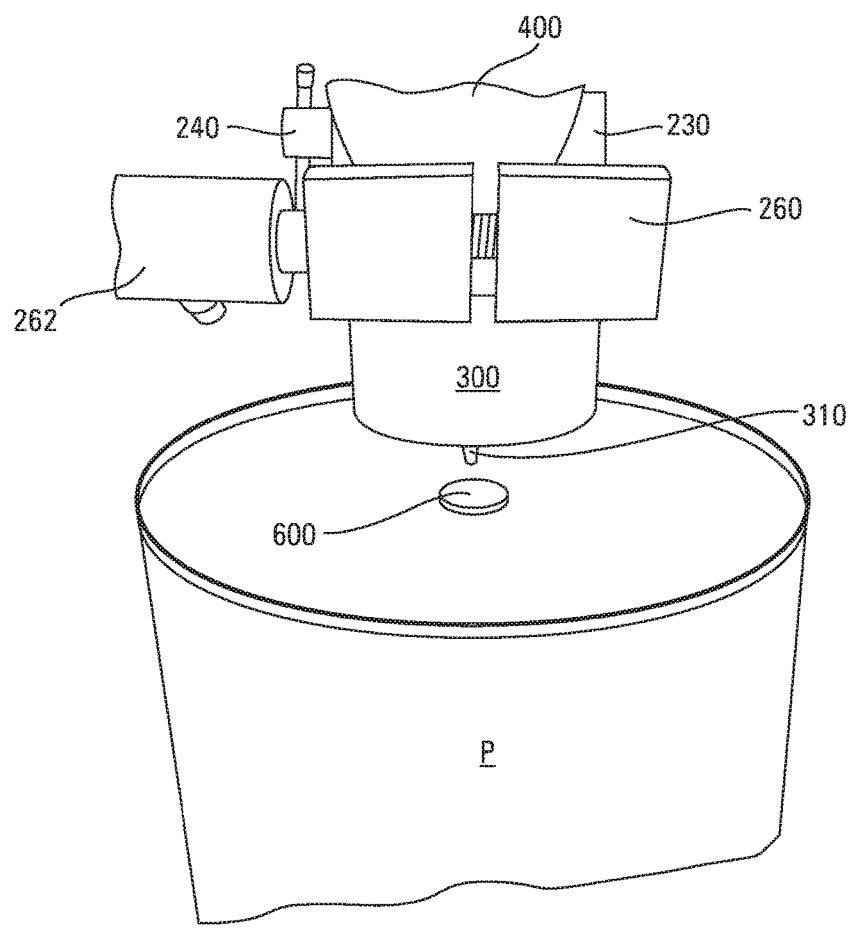
FIG. 5 is an enlarged front perspective view of the clamp portion of the mechanical punch press depicted in FIG. 4 providing a view of a septum adhered to the rigid package.

Referring to FIGS. 5 and 8, in order to prevent the introduction of atmospheric oxygen into the packaging P or S when the packaging P or S is punctured or pierced, an elastomeric septum 600 may be adhered to the package P or S through which the piercing member 310 on the fixture 300 or the needle 420 on the oxygen analyzer 400 is then inserted into the packaging P or S respectively.

I claim:

1. An assembly, comprising:
    (a) a first component comprising a mechanical punch press equipped with a longitudinally reciprocable fixture having a sharp-tipped, rigid, lumen defining, hollow piercing member extending in a first longitudinal direction from the fixture, and a longitudinal bore extending completely through the fixture and into fluid communication with the lumen of the piercing member, and
    (b) a second component comprising an oxygen analyzer having an oxygen sensitive luminescent sensor retained within a rigid, lumen defining, hollow, side-port needle proximate a distal end of the needle, with the fixture and the oxygen analyzer configured and arranged relative to one another for sealed, detachable, mounting of the oxygen analyzer onto the fixture with the needle extending into the bore of the fixture with the distal tip of the needle positioned within the lumen of the piercing member,
    (c) wherein (—) the assembly is operable, when the first and second components are assembled, as a benchtop instrument for sealed penetration of the oxygen sensitive luminescent sensor into sensible communication with an enclosed space of a sealed rigid package, and (—) the oxygen analyzer component of the assembly is operable, when the first and second components are disassembled, as a handheld instrument for sealed penetration of the oxygen sensitive luminescent sensor into sensible communication with an enclosed space of a flexible package.

2. The assembly of claim 1 wherein the fixture is releasably attached to the mechanical punch press by a clamp.

3. The assembly of claim 2 wherein the mechanical punch press is a self-standing bench punch press having a base, a vertical support post upon which the clamp is reciprocably mounted, and a manually actuatable lever for effecting reciprocation of the clamp as between a rest position further from the base and a working position closer to the base.

4. The assembly of claim 3 wherein the reciprocable clamp is a clamping collar.

5. A method of serially measuring oxygen concentration inside each of a sealed rigid package and a sealed flexible package, comprising the steps of:
    (a) obtaining an assembly in accordance with claim 3,
    (b) piercing the rigid package with the piercing member by actuation of the mechanical punch press so as to cause the piercing member to penetrate into the sealed rigid package with the fixture sealingly engaging the sealed rigid package, (c) allowing the oxygen concentration in sensing communication with the oxygen sensitive luminescent sensor to equilibrate with the oxygen concentration in the sealed rigid package,
(d) activating the oxygen analyzer whereby the oxygen analyzer optically interrogates the oxygen sensitive luminescent sensor to obtain a value representative of the partial pressure of oxygen in the sealed rigid package,
(e) converting the obtained value to an oxygen concentration based upon a known conversion algorithm, and
(f) visually reporting the oxygen concentration,
(g) disassembling the first and second components and thereafter,
(h) piercing the flexible package with the needle of the oxygen analyzer,
(i) allowing the oxygen concentration in sensing communication with the oxygen sensitive luminescent sensor to equilibrate with the oxygen concentration in the sealed flexible package,
(j) activating the oxygen analyzer whereby the oxygen analyzer optically interrogates the oxygen sensitive luminescent sensor to obtain a value representative of the partial pressure of oxygen in the sealed flexible package,
(k) converting the obtained value to an oxygen concentration based upon a known conversion algorithm, and
(l) visually reporting the oxygen concentration.

6. A method of serially measuring oxygen concentration inside each of a sealed rigid package and a sealed flexible package, comprising the steps of:
(a) obtaining an assembly in accordance with claim 3,
(b) adhering a septum to the exterior of the rigid package,
(c) piercing the rigid package with the piercing member by actuation of the mechanical punch press so as to cause the piercing member to penetrate through the septum and into the sealed rigid package with the fixture sealingly engaged against the septum,
(d) allowing the oxygen concentration in sensing communication with the oxygen sensitive luminescent sensor to equilibrate with the oxygen concentration in the sealed rigid package,
(e) activating the oxygen analyzer whereby the oxygen analyzer optically interrogates the oxygen sensitive luminescent sensor to obtain a value representative of the partial pressure of oxygen in the sealed rigid package,
(f) converting the obtained value to an oxygen concentration based upon a known conversion algorithm,
(g) visually reporting the oxygen concentration,
(h) disassembling the first and second components and thereafter,
(i) piercing the flexible package with the needle of the oxygen analyzer,
(j) allowing the oxygen concentration in sensing communication with the oxygen sensitive luminescent sensor to equilibrate with the oxygen concentration in the sealed flexible package,
(k) activating the oxygen analyzer whereby the oxygen analyzer optically interrogates the oxygen sensitive luminescent sensor to obtain a value representative of the partial pressure of oxygen in the sealed flexible package,
(l) converting the obtained value to an oxygen concentration based upon a known conversion algorithm, and
(m) visually reporting the oxygen concentration.

7. A method of serially measuring oxygen concentration inside each of a sealed rigid package and a sealed flexible package, comprising the steps of:
(a) obtaining an assembly in accordance with claim 3,
(b) placing the rigid package upon the base of the mechanical punch press,
(c) adhering a septum to an upward facing exterior surface of the rigid package,
(d) manually actuating the lever of the mechanical punch press to move the reciprocable clamp and thereby the fixture retained by the reciprocable clamp towards the septum until the piercing member penetrates through the septum and into the sealed rigid package with the fixture sealingly engaging the septum,
(e) allowing the oxygen concentration in sensing communication with the oxygen sensitive luminescent sensor to equilibrate with the oxygen concentration in the sealed rigid package,
(f) activating the oxygen analyzer whereby the oxygen analyzer optically interrogates the oxygen sensitive luminescent sensor to obtain a value representative of the partial pressure of oxygen in the sealed rigid package,
(g) converting the obtained value to an oxygen concentration based upon a known conversion algorithm, and
(h) visually reporting the oxygen concentration, and
(i) disassembling the first and second components and thereafter,
(j) adhering a septum to an upward facing exterior surface of the flexible package,
(k) piercing the flexible package with the needle of the oxygen analyzer through the septum,
(l) allowing the oxygen concentration in sensing communication with the oxygen sensitive luminescent sensor to equilibrate with the oxygen concentration in the sealed flexible package,
(m) activating the oxygen analyzer whereby the oxygen analyzer optically interrogates the oxygen sensitive luminescent sensor to obtain a value representative of the partial pressure of oxygen in the sealed flexible package,
(n) converting the obtained value to an oxygen concentration based upon a known conversion algorithm, and
(o) visually reporting the oxygen concentration.

8. The assembly of claim 1 wherein the piercing member longitudinally extends between 0.5 and 2 cm from the fixture.

9. The assembly of claim 1 wherein the fixture has a volume of 50 to 100 cm$^3$ inclusive of internal void volume.

10. The assembly of claim 1 wherein the oxygen sensitive luminescent sensor includes an oxygen sensitive porphyrin dye retained within an oxygen permeable matrix, and the oxygen analyzer is a fiber optic oxygen analyzer further equipped with a source of excitation energy and a detector for sensing and measuring luminescent energy emitted by the oxygen sensitive porphyrin dye when excited.

* * * * *